United States Patent
Saiyed et al.

(10) Patent No.: US 9,304,122 B2
(45) Date of Patent: Apr. 5, 2016

(54) MICROFLUIDIC-BASED FLOW ANALYZER

(71) Applicant: CENTRE FOR CELLULAR AND MOLECULAR PLATFORMS (C-CAMP), Bangalore (IN)

(72) Inventors: Taslimarif Saiyed, Bangalore (IN); Sudip Mondal, Bangalore (IN); Anil Prabhakar, Chennai (IN); H. Krishnamurthy, Bangalore (IN)

(73) Assignee: CENTRE FOR CELLULAR AND MOLECULAR PLATFORMS (C-CAMP), Bangalore (IN)

( * ) Notice: Subject to any disclaimer, the term of this patent is extended or adjusted under 35 U.S.C. 154(b) by 108 days.

(21) Appl. No.: 14/376,507

(22) PCT Filed: Feb. 1, 2013

(86) PCT No.: PCT/IB2013/050871
§ 371 (c)(1),
(2) Date: Aug. 4, 2014

(87) PCT Pub. No.: WO2013/114333
PCT Pub. Date: Aug. 8, 2013

(65) Prior Publication Data
US 2014/0374630 A1    Dec. 25, 2014

(30) Foreign Application Priority Data
Feb. 4, 2012  (IN) ............ 4067/CHE/2011

(51) Int. Cl.
*G01N 33/49* (2006.01)
*G01N 15/14* (2006.01)
*B01L 3/00* (2006.01)
*G01N 21/53* (2006.01)

(52) U.S. Cl.
CPC ...... *G01N 33/4915* (2013.01); *B01L 3/502715* (2013.01); *G01N 15/1434* (2013.01);
(Continued)

(58) Field of Classification Search
CPC .......... G01N 33/4915; G01N 15/1436; G01N 15/1434; G01N 15/1484; G01N 21/53
USPC ......................................... 250/564, 574, 575
See application file for complete search history.

(56) References Cited

U.S. PATENT DOCUMENTS

| 6,906,797 | B1 | 6/2005 | Kao et al. |
| 2009/0053686 | A1* | 2/2009 | Ward ................. G01N 15/1404 435/2 |
| 2011/0037077 | A1 | 2/2011 | Ichimura et al. |

FOREIGN PATENT DOCUMENTS

JP    2006-184057    7/2006

*Primary Examiner* — Seung C Sohn
(74) *Attorney, Agent, or Firm* — Hamre, Schumann, Mueller & Larson, P.C.

(57) ABSTRACT

The present disclosure is related to a microfluidic flow analyzer for pathological detection. The microfluidic flow analyzer comprises plurality of buffer channels, sample channel, central flow channel, plurality of exciting optical channels and plurality of receiving optical channels. The plurality of exciting optical channels and the plurality of receiving optical channels are placed at predetermined angle to the central flow channel. The plurality of exciting optical channels excite cell in the sample solution flowing through the central flow channel. The cell being excited produces one or more optical signals. The one or more optical signals are received by the plurality of receiving optical channels. The microfluidic flow analyzer comprises plurality of detectors placed on each of the plurality of receiving optical channels for detecting one of the one or more optical signals. The detected optical signal is sent to a computing unit for pathological detection.

20 Claims, 10 Drawing Sheets

(52) U.S. Cl.
CPC ........ *G01N15/1436* (2013.01); *G01N 15/1484* (2013.01); *G01N 21/53* (2013.01); *B01L 2300/0654* (2013.01); *B01L 2300/0816* (2013.01); *B01L 2400/0487* (2013.01); *G01N 2015/1493* (2013.01)

MICROFLUIDIC-BASED FLOW ANALYZER

CROSS-REFERENCE TO RELATED APPLICATION

The present application claims priority to Indian patent application serial number 4067/CHE/2011 filed on Feb. 4, 2012, the entire contents of which are incorporated by reference.

TECHNICAL FIELD

The present disclosure is related to a microfluidic flow analyzer. In particular, the present disclosure relates to a microfluidic flow analyzer for pathological detection.

BACKGROUND

Human Immunodeficiency Virus (HIV) is one of the most serious infectious diseases with nearly 33.3 million infected individuals worldwide in the year 2009. Out of these infected individuals, 2.5 million are below 15 years of age with 14.6 million people estimated to be in need of antiretroviral therapy (ART). People with a cell count lower than 350 are usually administered with ART.

In Acquired immune deficiency syndrome (AIDS) patients, HIV causes a significant reduction in CD4 cells. CD4 cells initiate the body's immune response. Hence, an effective way to monitor AIDS is to measure CD4 cell proportion in blood samples of patients during the therapy for HIV. Patients need to be monitored every 3-6 months to verify the progression of the disease.

Currently, HIV diagnosis is carried out using Enzyme-linked immunesorbent assay (ELISA) or through conventional flow cytometry techniques. ELISA is a common qualitative technique used to diagnose HIV and it is an effective method of HIV detection. Conventionally, flow cytometers are used to measure the level of HIV infection by CD4 cell count which increases during the immune response. These bulky instruments are disadvantageous in that they require expensive chemicals, thorough maintenance and experienced medical professionals to operate and maintain them effectively. This makes AIDS diagnosis a very costly and cumbersome affair at the present time.

Hence, there exists a need for a cost effective system and technique for pathological detection.

SUMMARY

The shortcomings of the prior art are overcome and additional advantages are provided through the provision of a method and system as described in the description.

In an embodiment, the present disclosure provides a microfluidic flow analyzer for pathological detection. The microfluidic flow analyzer comprises plurality of buffer channels, a sample channel, a central flow channel, plurality of first exciting optical channels, plurality of first receiving optical channels, plurality of first detectors, wherein one or more second exciting optical channels, one or more second receiving optical channels and one or more second detectors. The plurality of buffer channels is configured to carry buffer solution and the sample channel is configured to carry sample solution. The central flow channel is configured to receive the buffer solution and the sample solution, wherein the plurality of buffer channels and the sample channel are converged at entry side of the central flow channel to form narrow path in the central flow channel for the sample solution to flow in the central flow channel. The plurality of first exciting optical channels is placed orthogonally to the central flow channel. Each of the plurality of first exciting optical channels is coupled with a first set of fibre coupled laser source to excite cells in the sample solution, flowing through the central flow channel, to produce one or more first optical signals. Each of the plurality of first receiving optical channels is placed at a predetermined angle to optical axis of each of the plurality of first exciting optical channels respectively, to receive the one or more first optical signals. Each of the plurality of first detectors placed on each of the plurality of first receiving optical channels detects at least one of the one or more first optical signals.

Each of the one or more second exciting optical channels is placed at a predetermined angle to the central flow channel. Each of the one or more second exciting optical channels is coupled with a second set of fibre coupled laser source to excite the cells in the sample solution, flowing through the central flow channel, to produce one or more second optical signals. Each of the one or more second receiving optical channels placed at a predetermined angle to the central flow channel is configured to receive the one or more second optical signals. Each of the one or more second detectors is placed on each of the one or more second receiving optical channels to detect at least one of the one or more second optical signals.

In an embodiment, the present disclosure provides a method for pathological detection using the microfluidic flow analyzer. The method comprises receiving buffer solution and sample solution by a central flow channel through plurality of buffer channels and a sample channel respectively, wherein the plurality of buffer channels and the sample channel are converged at entry side of the central flow channel to form narrow path in the central flow channel for the sample solution to flow in the central flow channel. Upon receiving the buffer solution and the sample solution by the central flow channel, cells in the sample solution flowing through the central flow channel are excited by plurality of first set of fibre coupled laser source to produce one or more first optical signals. The plurality of first set of fibre coupled laser source is respectively coupled to plurality of first exciting optical channels. The one or more first optical signals are received by plurality of first receiving optical channels. Upon receiving the one or more first optical signals, each of plurality of first detectors placed on each of the plurality of first receiving optical channels respectively detects one of the one or more first optical signals. The detected one of the one or more first optical signals is received by the computing unit for pathological detection. The method also comprises exciting cells in the sample solution by a plurality of second set of fibre coupled laser source to produce one or more second optical signals, wherein the plurality of second set of fibre coupled laser source is respectively coupled to one or more second exciting optical channels. The one or more second optical signals are received by plurality of second receiving optical channels. Upon receiving the one or more first second signals, each of plurality of second detectors placed on each of the plurality of second receiving optical channels respectively, detects one of the one or more second optical signals. The detected one of the one or more second optical signals is received by the computing unit for pathological detection.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure. In an embodiment, the present disclosure provides a microfluidic flow analyzer for pathological detection.

Figure 1:
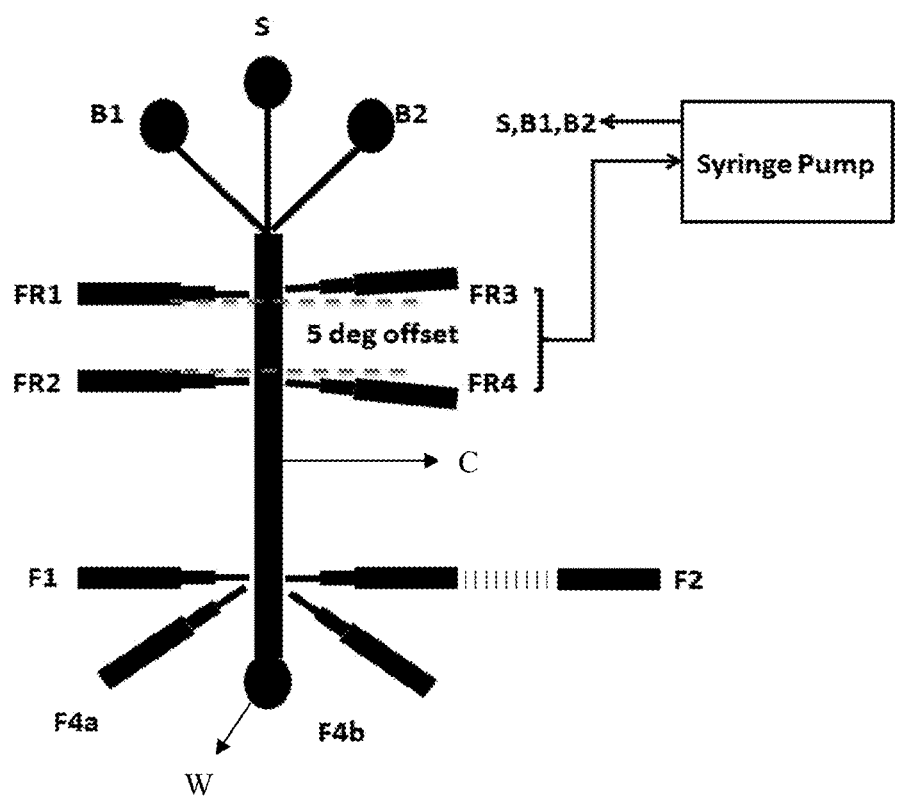
FIG. 1 illustrates schematic design of a microfluidic flow analyzer for pathological detection in accordance with an embodiment of the present disclosure.

FIG. 1 illustrates a schematic design of a microfluidic flow analyzer for pathological detection in accordance with an embodiment of the present disclosure. The microfluidic flow analyzer comprises plurality of buffer channels (B1, B2), a sample channel (S), a central flow channel (C), a waste reservoir (W), plurality of first exciting optical channels (FR1, FR2), plurality of first receiving optical channels (FR3, FR4), plurality of first detectors (not shown in figure), one or more second exciting optical channels (F1, F4a), one or more second receiving optical channels (F2, F4b) and one or more second detectors (not shown in figures). Each of the plurality of buffer channels (B1 and B2) is configured to carry buffer solution and the sample channel (C) is configured to carry sample solution. The buffer solution includes, but are not limited to, water, fluorescein solution, serum, Phosphate buffered saline (PBS) and other saline buffers. The sample solution may include, but are not limited to, blood cells, single cells from culture cell lines, serum, bacteria, contaminants in pure liquid and fluorescently labeled cells. The central flow channel (C) is configured to receive the buffer solution and the sample solution from the plurality of buffer channels (B1, B2) and the sample channel (S) respectively. The plurality of buffer channels (B1, B2) and the sample channel (S) are converged at entry side of the central flow channel (C) to form narrow path in the central flow channel (C) for the sample solution to flow in the central flow channel (C). The narrow path for the sample channel (S) allows linear movement of each cell in the sample solution. In an embodiment, the plurality of buffer channels (B1, B2) and the sample channel (S) is configured in a microfluidic chip. The waste reservoir (W) is configured at exit side of the central flow channel (C) to collect samples after analysis from the central flow channel.

In an embodiment, each of the plurality of the buffer channels (B1, B2) and the sample channel (S) is coupled with an infusion pump to control the flow of the buffer solution and the sample solution flowing through the plurality of buffer channels (B1, B2) and the sample channel (S) respectively. The infusion pump coupled to each of the plurality of buffer channels (B1, B2) and the sample channel (C) is connected to a computing device. Each of the plurality of first exciting optical channels (FR1, FR2) is placed orthogonally to the central flow channel. Each of the plurality of first exciting optical channels (FR1, FR2) is coupled with a first set of fibre coupled laser source. The first set of fibre coupled laser source is terminated at a lensed fibre. Each of the plurality of first receiving optical channels (FR3, FR4) is placed at a predetermined angle to optical axis of each of the plurality of first exciting optical channels (FR1, FR2) respectively. In an embodiment, the predetermined angle at which each of the plurality of first receiving optical channels (FR3, FR4) is placed at an angle of ±5 degrees to the optical axis of each of the plurality of first exciting optical channels respectively (FR1, FR2).

The first set of fibre coupled laser source coupled to each of the plurality of first exciting optical channels (FR1, FR2) excites cell in the sample solution (S), flowing through the central flow channel (C). The cell being excited produces one or more first optical signals. The one or more first optical signals are at least one of signal scattered in a forward direction from the cell being excited, signal scattered in any other direction other than the forward direction from the cell being excited and fluorescence signal emitted from the cell being excited. Each of the plurality of first receiving optical channels (FR3, FR4) receives the one or more first optical signals produced by the cell being excited.

In an embodiment, each of the plurality of first detectors is placed on each of the plurality of first receiving optical channels (FR3, FR4). The plurality of first detectors are at least one of a fibre coupled Indium gallium arsenide (InGaAs) detector, Silicon-Photomultiplier (Si-PMT) based photo detector, silicon based photo detector and silicon avalanche photo diode. The first detector placed on FR3 detects one of the one or more first optical signals. The one of the one or more first optical signals detected by the first optical detector is the signal scattered in the forward direction from the cell being excited. The first detector placed on FR3 sends the detected one of the one or more first optical signals to a computing unit. The computing unit analyzes the signal scattered in the forward direction from the cell being excited for pathological detection. The intensity of the signal scattered in the forward direction from the cell being excited is approximately proportional to cell size or diameter. The first detector placed on FR4 detects one of the one or more first optical signals. The one of the one or more first optical signals detected by the first optical detector is the signal scattered in the forward direction from the cell being excited. The first detector placed on FR4 sends the detected one of the one or more first optical signals to the computing unit. The computing unit analyzes the signal scattered in the forward direction from the cell being excited for pathological detection. The control feedback from the plurality of first receiving optical channels (FR3, FR4) is used to control a syringe pump which in turn controls the flow rates of the buffer solution and the sample solution.

In an embodiment, each of the one or more second exciting optical channels (F1, F4a) is placed at a predetermined angle to the central flow channel (C). For example, F1 is placed orthogonally to the central flow channel (C) and F4a is placed at an angle of 45 degrees to the central flow channel (C). Each of the one or more second exciting optical channels (F1, F4a) is coupled with a second set of fibre coupled laser source to excite the cells in the sample solution. The second set of fibre coupled laser source is terminated at a lensed fibre. The second exciting optical channel F1 is coupled with a second set of fibre coupled laser source terminated at a lensed fibre and the second exciting optical channel F4a is coupled with a second set of fibre coupled laser source terminated at a lensed fibre. The second set of fibre coupled laser source coupled to each of the one or more second exciting optical channels F1 and F4a excites the cell in the sample solution to produce one or more second optical signals. The one or more second optical signals are at least one of signal scattered in a forward direction from the cell being excited, signal scattered in any other direction other than the forward direction from the cell being excited and fluorescence signal emitted from the cell being excited.

Each of the one or more second receiving optical channels (F2, F4b) receives the one or more second optical signals. Each of the one or more second receiving optical channels (F2, F4b) is placed at a predetermined angle to the central flow channel (C). F2 is placed orthogonally to the central flow channel (C) and F4b is placed at an angle of 45 degrees to the central flow channel (C). The optical axis of both F1 and F2 are same. The microfluidic flow analyzer further comprises one or more second detectors, wherein each of the one or more second detectors is placed on each of the one or more second receiving optical channels (F2, F4b). The plurality of second detectors are at least one of a fibre coupled Indium gallium arsenide (InGaAs) detector, Silicon-Photomultiplier (Si-PMT) based photo detector, silicon based photo detector and silicon avalanche photo diode. Each of the one or more second detectors detects one of the one or more second optical signals. The second detector placed at F2 detects the fluorescence signal emitted from the cell being excited and sends the detected fluorescence signal to the computing unit. The computing unit analyzes the fluorescence signal for pathological detection. The second detector placed at F4b detects the signal scattered in any other direction other than the forward direction from the cell being excited and sends the detected signal to the computing unit. The computing unit analyzes the signal scattered in any other direction other than the forward direction from the cell being excited for pathological detection. In an embodiment, one of the one or more second receiving optical channels is configured with a Fibre Bragg grating to filter laser light emitted from each of the one or more second exciting optical channels (F1, F4a). As an example, F2 is configured with the Fibre Bragg grating.

Figure 2:
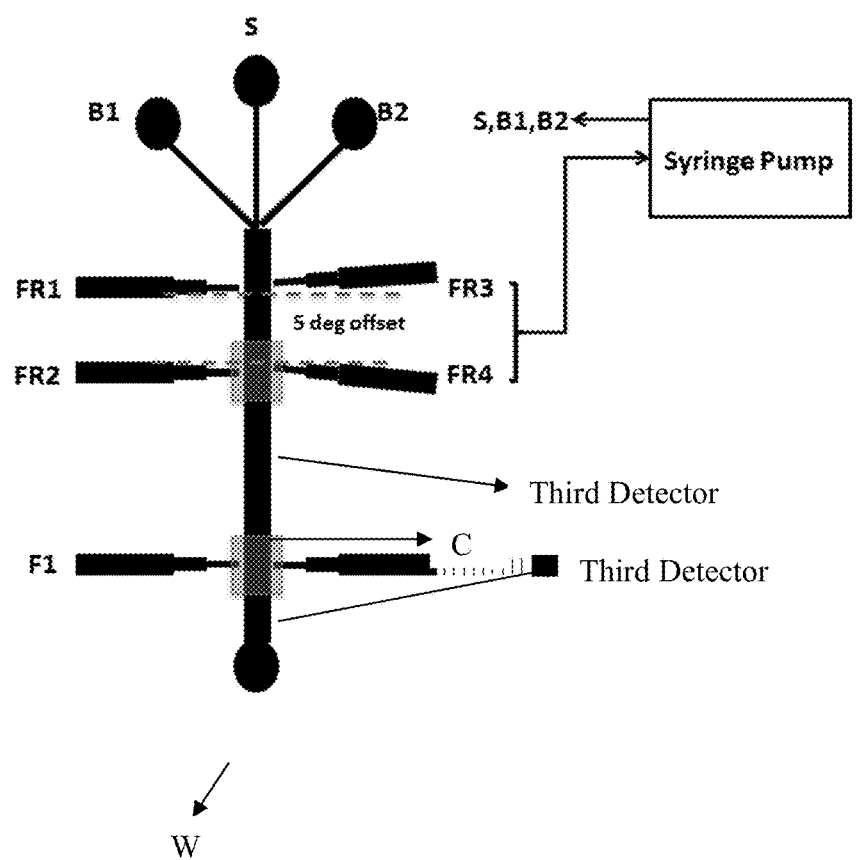
FIG. 2 illustrates an exemplary schematic design of a microfluidic flow analyzer for pathological detection in accordance with another embodiment of the present disclosure.

FIG. 2 illustrates schematic design of a microfluidic flow analyzer for pathological detection in accordance with another embodiment of the present disclosure. The microfluidic flow analyzer comprises two buffer channels (B1, B2) and a sample channel (S). The buffer channels (B1, B2) and the sample channel (S) are converged at entry side of the central flow channel (C). The microfluidic flow analyzer comprises plurality of first exciting optical channels (FR1, FR2) placed orthogonally to the central flow channel (C). The first set of fibre coupled laser source coupled to each of the plurality of first exciting optical channels (FR1, FR2) excites cell in the sample solution, flowing through the central flow channel (C) to produce one or more first optical signals. The microfluidic flow analyzer comprises plurality of first receiving optical channels (FR3, FR4) placed at a predetermined angle to optical axis of each of the plurality of first exciting optical channels (FR1, FR2) respectively, to receive the one or more first optical signals. The process of pathological detection by the microfluidic flow analyzer using the optical channels FR1, FR2, FR3 and FR4 is as illustrated in FIG. 1

The microfluidic flow analyzer comprises one or more second exciting optical channels. In this embodiment, the microfluidic flow analyzer comprises single second exciting optical channel (F1), which is placed at a predetermined angle to the central flow channel. For example, the F1 is placed orthogonally to the central flow channel (C). Further, the F1 is coupled with a second set of fibre coupled laser source to excite the cells in the sample solution. The second set of fibre coupled laser source is terminated at a lensed fibre. The second set of fibre coupled laser source coupled to the F1 excites the cell in the sample solution to produce one or more second optical signals. The one or more second optical signals are at least one of signal scattered in a forward direction from the cell being excited, signal scattered in any other direction other than the forward direction from the cell being excited and fluorescence signal emitted from the cell being excited.

The microfluidic flow analyzer comprises one or more second receiving optical channels to receive the one or more second optical signals. In this embodiment, the microfluidic flow analyzer comprises single second receiving optical channel (F2), which is placed orthogonally to the central flow channel (C). Further, the optical axis of both the F1 and the F2 are same. The microfluidic flow analyzer comprises one or more second detectors, wherein each of the one or more second detectors is placed on the second receiving optical channel (F2). The plurality of second detectors are at least one of a fibre coupled Indium gallium arsenide (InGaAs) detector, Silicon-Photomultiplier (Si-PMT) based photo detector, silicon based photo detector and silicon avalanche photo diode. Each of the one or more second detectors detects one of the one or more second optical signals. The second detector placed at F2 detects the fluorescence signal emitted from the cell being excited and sends the detected fluorescence signal to the computing unit. The computing unit analyzes the fluorescence signal for pathological detection. In an embodiment, F2 is configured with a Fibre Bragg grating to filter laser light emitted from the second exciting optical channel (F1).

The microfluidic flow analyzer also comprises plurality of third detectors. Each of the plurality of third detectors is placed at intersection of central axis of the central flow channel (C) and optical axis of one of the plurality of first exciting optical channels, to detect one of the one or more first optical signals scattered in any other direction other than forward direction from the cells being excited. The third detector is placed at the intersection of central axis of the central flow channel and the optical axis of the FR2. The third detector detects the optical signal scattered in any other direction other than the forward direction from the cell being excited. The third detector sends the detected optical signal to the computing unit, wherein the computing unit analyzes the signal scattered in any other direction other than the forward direction from the cell being excited for pathological detection. Each of the third detectors is placed at the intersection of central axis of the central flow channel and optical axis of one of the one or more second exciting optical channels, to detect one of the one or more second optical signals scattered in any other direction other than forward direction from the cells being excited.

One more third detector is also placed at the intersection of central axis of the central flow channel (C) and the optical axis of the F1. The third detector detects the optical signal scattered in any other direction other than the forward direction from the cell being excited. The third detector sends the detected optical signal to the computing unit, wherein the computing unit analyzes the signal scattered in any other direction other than the forward direction from the cell being excited for pathological detection.

Figure 3:
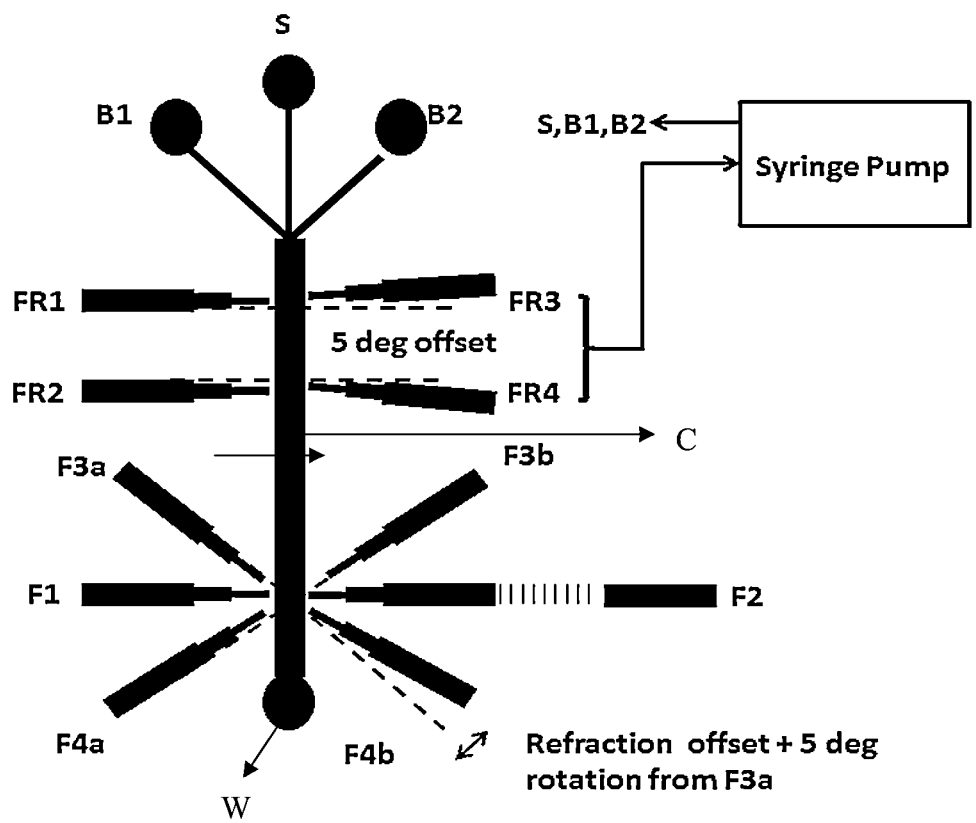
FIG. 3 illustrates an exemplary schematic design of a microfluidic flow analyzer for pathological detection in accordance with another embodiment of the present disclosure.

FIG. 3 illustrates schematic design of a microfluidic flow analyzer for pathological detection in accordance with an example embodiment of the present disclosure. The microfluidic flow analyzer comprises two buffer channels (B1, B2) and the sample channel (S). The buffer channels (B1, B2) and the sample channel (S) are converged at entry side of the central flow channel (C). The microfluidic flow analyzer comprises plurality of first exciting optical channels (FR1, FR2) placed orthogonally to the central flow channel (C). The first set of fibre coupled laser source coupled to each of the plurality of first exciting optical channels (FR1, FR2) excites cell in the sample solution, flowing through the central flow channel (C) to produce one or more first optical signals. The microfluidic flow analyzer comprises plurality of first receiving optical channels (FR3, FR4) placed at a predetermined angle to optical axis of each of the plurality of first exciting optical channels (FR1, FR2) respectively, to receive the one or more first optical signals. The process of pathological detection by the microfluidic flow analyzer using the optical channels FR1, FR2, FR3 and FR4 is as illustrated in FIG. 1.

The microfluidic flow analyzer comprises one or more second exciting optical channels (F1, F3a, and F4a). Each of the one or more second exciting optical channels (F1, F3a, and F4a) is placed at a predetermined angle to the central flow channel (C). F1 is placed orthogonally to the central flow channel (C) and F3a and F4a are placed at an angle of 45 degrees to the central flow channel (C). F1, F3a and F4a are coupled with a second set of fibre coupled laser source to excite the cells in the sample solution. F1 is coupled with a second set of fibre coupled laser source terminated at a lensed fibre. F3a is coupled with a second set of fibre coupled laser source terminated at a lensed fibre. F4a is coupled with a second set of fibre coupled laser source terminated at a lensed fibre. Each of the second set of fibre coupled laser source coupled to each of the plurality of second exciting optical channels F1, F3a and F4a excites the cell in the sample solution to produce one or more second optical signals. The one or more second optical signals are at least one of signal scattered in a forward direction from the cell being excited, signal scattered in any other direction other than the forward direction from the cell being excited and fluorescence signal emitted from the cell being excited.

Figure 4:
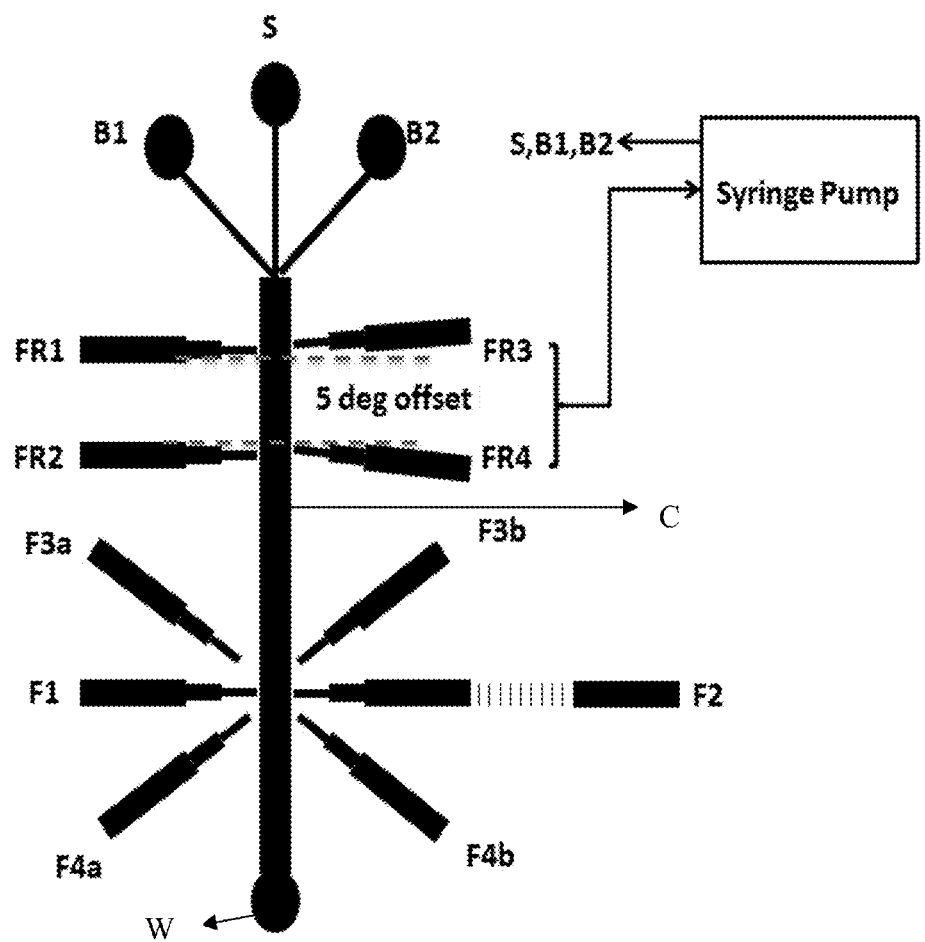
FIG. 4 illustrates an exemplary schematic design of a microfluidic flow analyzer for pathological detection in accordance with another embodiment of the present disclosure.

The microfluidic flow analyzer comprises one or more second receiving optical channels (F2, F3b, and F4b) to receive the one or more second optical signals. For example, F2 is placed orthogonally to the central flow channel (C). F3b is placed at an angle of 45 degrees to the central flow channel (C) and F4b is placed at an angle of ±40 degrees to the central flow channel (C). In the alternative embodiment, the F4b is placed at an angle of 45 degrees to the central flow channel (C) as shown in FIG. 4. The microfluidic flow analyzer comprises one or more second detectors, wherein each of the one or more second detectors is placed on each of the one or more second receiving optical channels (F2, F3b and F4b). The plurality of second detectors are at least one of a fibre coupled Indium gallium arsenide (InGaAs) detector, Silicon-Photomultiplier (Si-PMT) based photo detector, silicon based photo detector and silicon avalanche photo diode. Each of the one or more second detectors detects one of the one or more second optical signals. The second detector placed at F2 detects the fluorescence signal emitted from the cell being excited and sends the detected fluorescence signal to the computing unit. The computing unit analyzes the fluorescence signal for pathological detection. In an embodiment, F2 is configured with a Fibre Bragg grating to filter laser light emitted from each of the one or more second exciting optical channels. The second detector placed at F3b detects the signal scattered in any other direction other than the forward direction from the cell being excited and sends the detected signal to the computing unit. The computing unit analyzes the signal scattered in any other direction other than the forward direction from the cell being excited for pathological detection. The second detector placed at F4b detects the signal scattered in any other direction other than the forward direction from the cell being excited and sends the detected signal to the computing unit. The computing unit analyzes the signal scattered in any other direction other than the forward direction from the cell being excited for pathological detection.

Figure 5:
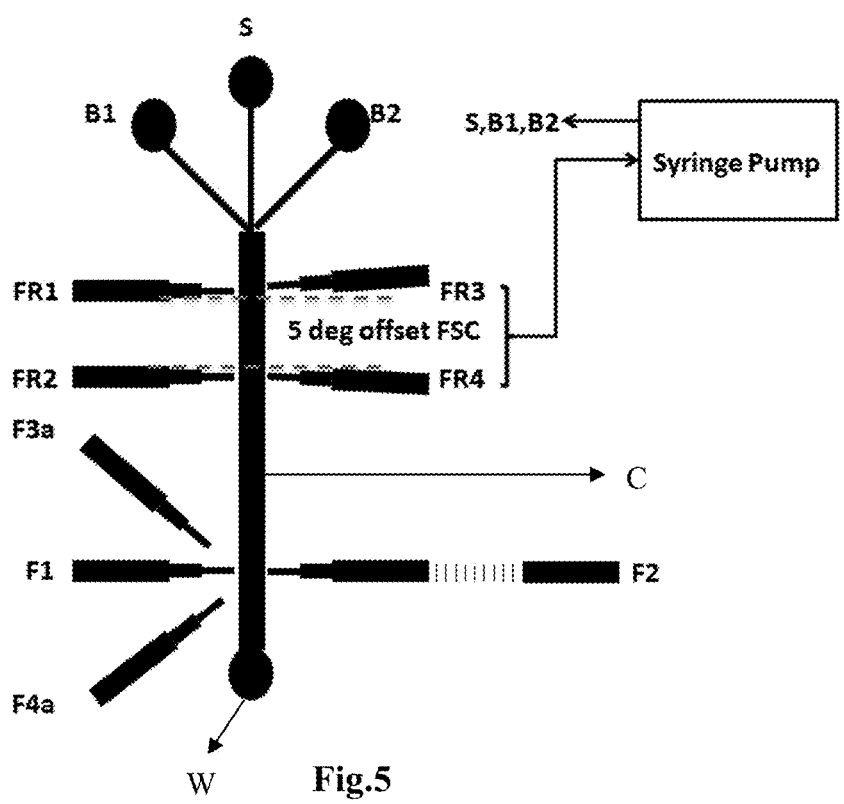
FIG. 5 illustrates an exemplary schematic design of a microfluidic flow analyzer for pathological detection in accordance with another embodiment of the present disclosure.

FIG. 5 illustrates schematic design of a microfluidic flow analyzer for pathological detection in accordance with an example embodiment of the present disclosure. The microfluidic flow analyzer comprises two buffer channels (B1, B2) and the sample channel (S). The buffer channels (B1, B2) and the sample channel (S) are converged at entry side of the central flow channel (C). The microfluidic flow analyzer comprises plurality of first exciting optical channels (FR1, FR2) placed orthogonally to the central flow channel (C). The first set of fibre coupled laser source coupled to each of the plurality of first exciting optical channels (FR1, FR2) excites cell in the sample solution, flowing through the central flow channel (C) to produce one or more first optical signals. The microfluidic flow analyzer comprises plurality of first receiving optical channels (FR3, FR4) placed at a predetermined angle to optical axis of each of the plurality of first exciting optical channels (FR1, FR2) respectively, to receive the one or more first optical signals. The process of pathological detection by the microfluidic flow analyzer using the optical channels FR1, FR2, FR3 and FR4 is as illustrated in FIG. 1

The microfluidic flow analyzer comprises one or more second exciting optical channels (F1, F3a and F4a). Each of the one or more second exciting optical channels (F1, F3a and F4a) is placed at a predetermined angle to the central flow channel (C). F1 is placed orthogonally to the central flow channel (C) and F3a and F4a are placed at an angle of 45 degrees to the central flow channel (C). F1, F3a and F4a are coupled with a second set of fibre coupled laser source to excite the cells in the sample solution. F1 is coupled with a second set of fibre coupled laser source terminated at a lensed fibre. F3a is coupled with a second set of fibre coupled laser source terminated at a lensed fibre. F4a is coupled with a second set of fibre coupled laser source terminated at a lensed fibre. Each of the second set of fibre coupled laser source coupled to each of the plurality of second exciting optical channels (F1, F3a and F4a) excites the cell in the sample solution to produce one or more second optical signals. The one or more second optical signals are at least one of signal scattered in a forward direction from the cell being excited, signal scattered in any other direction other than the forward direction from the cell being excited and fluorescence signal emitted from the cell being excited.

The microfluidic flow analyzer comprises one or more second receiving optical channels to receive the one or more second optical signals. In this embodiment, the microfluidic flow analyzer comprises single second receiving optical channel (F2), which is placed orthogonally to the central flow channel (C). The microfluidic flow analyzer comprises one or more second detectors, wherein each of the one or more second detectors is placed on each of the one or more second receiving optical channels. The one or more second detectors are at least one of a fibre coupled Indium gallium arsenide (InGaAs) detector, Silicon-Photomultiplier (Si-PMT) based photo detector, silicon based photo detector and silicon avalanche photo diode. Each of the one or more second detectors detects one of the one or more second optical signals. The second detector placed at F2 detects the fluorescence signal emitted from the cell being excited and sends the detected fluorescence signal to the computing unit. The computing unit analyzes the fluorescence signal for pathological detection. In an embodiment, F2 is configured with a Fibre Bragg grating to filter laser light emitted from each of the one or more second exciting optical channels.

In one embodiment, the signal scattered in the forward direction from the cell being excited provides information on size and viability of the cells in the sample solution. The signal scattered in any other direction other than the forward direction from the cell being excited provides information on surface roughness and internal structures of cells such as granularity. The fluorescence signal is for quantifying specific markers that are stained onto the cells.

Figure 6A:
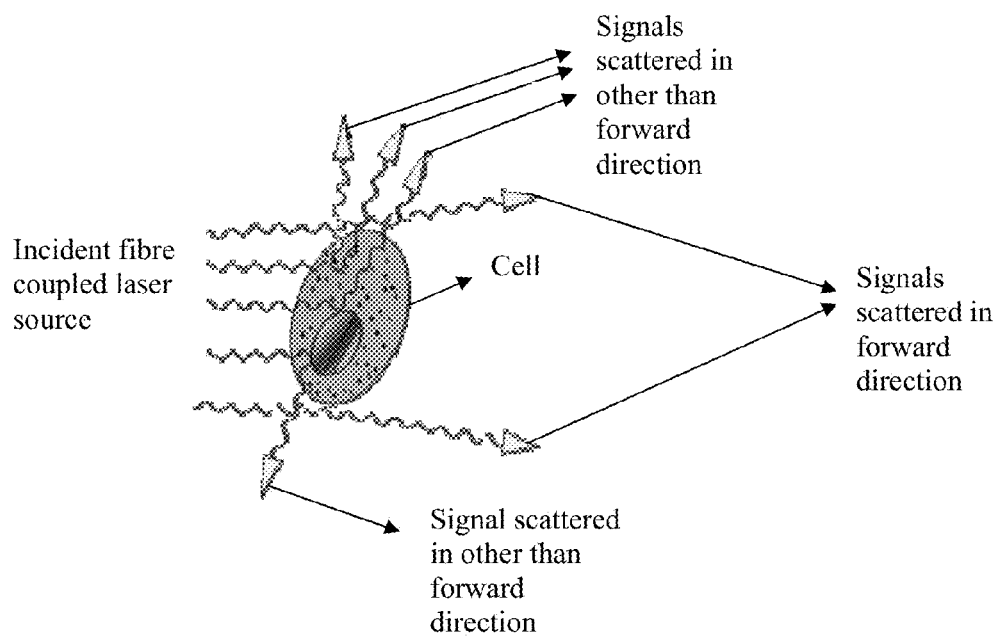
FIG. 6a shows one or more optical signals produced from the cell being excited.
Figure 6B:
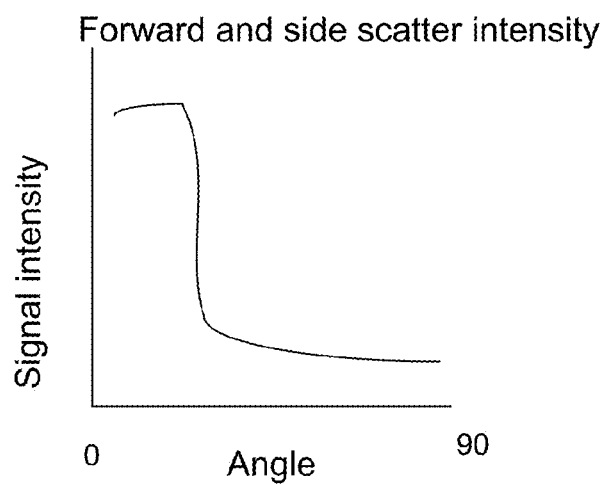
FIG. 6b shows a graph of intensity of one or more optical signals being produced when the cell is excited through one or more exciting optical channels placed at predetermined angles.

FIG. 6a shows one or more optical signals produced from the cell being excited. When the cell in the sample solution is excited by a fibre coupled laser source, the cell produces one or more optical signals. The one or more optical signals are the signal scattered in the forward direction from the cell being excited and the signal scattered in any other direction (right angle direction) other than the forward direction from the cell being excited. The one or more optical signal produced will have the same wavelength as the fibre coupled laser source. The intensity of the one or more optical signals produced is high at low angles and low at high angles as shown in FIG. 6b. The intensity of the signal scattered in the forward direction from the cell being excited is approximately proportional to cell size or diameter, while intensity of the signal scattered in any other direction other than the forward direction from the cell being excited is approximately proportional to quantity of granular structures within the cell or cell surface complexity.

In one embodiment, the signal scattered in the forward direction from the cell being excited (FS) and signal scattered in any other direction other than the forward direction from the cell being excited (LS) are used to discriminate between human lymphocytes, monocytes and granulocytes in a blood sample. Lymphocytes being smaller and granular they exhibit low FS and LS. Neutrophils are big and granular exhibiting high FS and LS. Monocytes stand in between the lymphocytes and Neutrophils.

Figure 7:
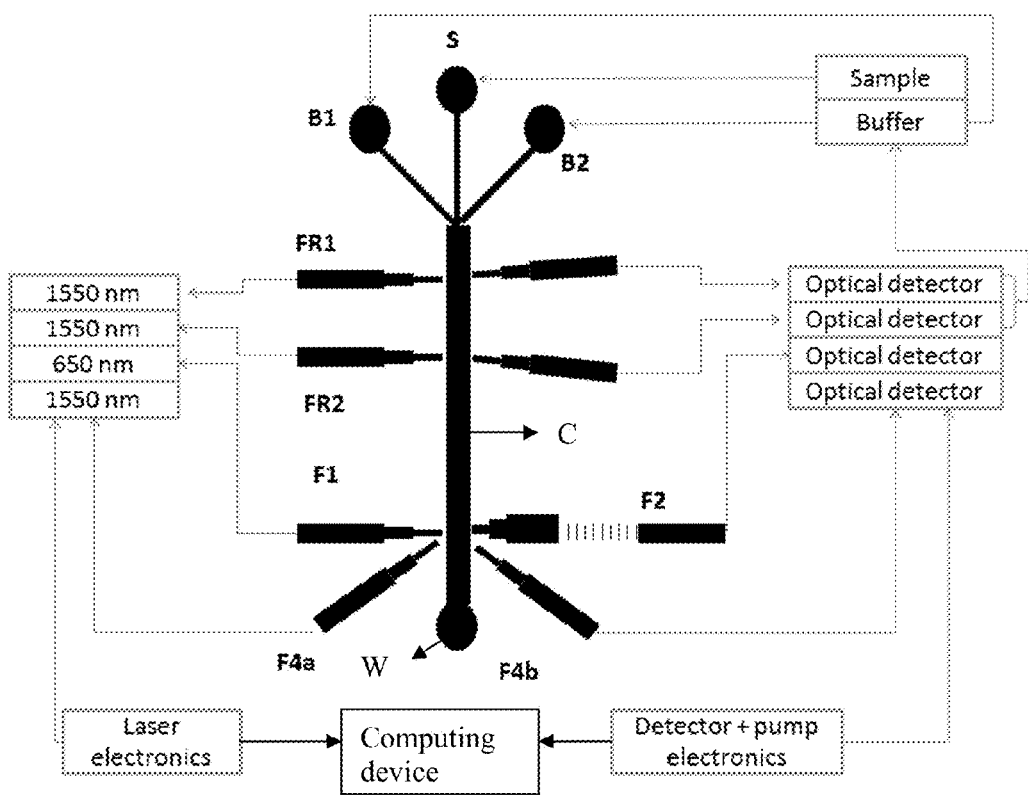
FIG. 7 illustrates system diagram for pathological detection in accordance with an embodiment of the present disclosure.

FIG. 7 illustrates a system diagram for pathological detection in accordance with an embodiment of the present disclosure. The system comprises a microfluidic flow analyzer, laser electronics, a computing device, detector and pump electronics and plurality of infusion pumps. The microfluidic flow analyzer comprises plurality of buffer channels (B1, B2), a sample channel (S), a central flow channel (C), a waste reservoir (W) and the plurality of optical channels (FR1, FR2, FR3, FR4, F1, F2, F4a and F4b) placed at predetermined angles to the central flow channel (C). Each of the plurality of infusion pumps is coupled to each of the plurality of buffer channels (B1, B2) and the sample channel (S). The infusion pumps control the flow of buffer solution and the sample solution flowing through the plurality of buffer channels (B1, B2) and the sample channel (S) respectively. Each of the plurality of infusion pumps is controlled by the detector and the pump electronics, wherein the detector and the pump electronics provides required buffer solution and the sample solution for the analysis. FR1 and FR2 are used to excite the cell in the sample solution flowing through the central flow channel (C), wherein the excited cell produces one or more first optical signals. FR3 and FR4 are used to receive the one or more first optical signals produced by the cell being excited. F1 and F4a are used to excite cells in the sample solution flowing through the central flow channel (C), wherein the excited cell produces one or more second optical signals. F2 and F4b are used to receive the one or more second optical signals produced by the cell being excited. The laser electronics comprises first set of fibre coupled laser source and a second set of fibre coupled laser source. The first set of fibre coupled laser source are terminated at a lensed fibre and coupled to FR1 and FR2 and the second set of fibre coupled laser source are terminated at a lensed fibre and coupled to F1 and F4a. The laser electronics controls the wavelength of the laser to be used for exciting the cells in the sample solution. At least one first optical detector is placed on FR3 and FR4 to detect at least one of one or more first optical signals. The detected at least one of the one or more optical signals is sent to the computing device. The computing device analyzes the received detected signal for pathological detection. At least one second optical detector is placed on F2 and F4b to detect at least one of one or more second optical signals. The detected at least one of the one or more second optical signals is sent to the computing device. The computing device analyzes the received detected signal for pathological detection. The detector and the pump electronics control the first and the second optical detectors.

Figure 8:
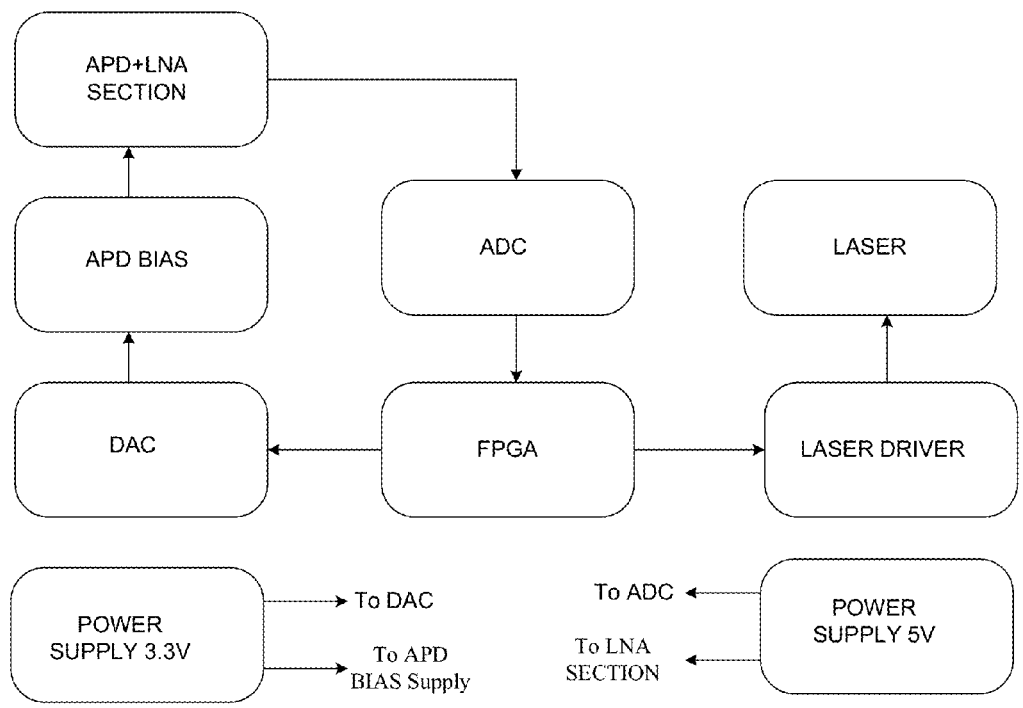
FIG. 8 illustrates block diagram of a hardware system to detect and analyze optical signals produced from the cell being excited.

FIG. 8 illustrates block diagram of a hardware system to detect and analyze optical signals produced from a cell being excited. As an example, the microfluidic flow analyzer uses an Avalanche Photo Diode (APD) as the optical detector to detect one of the one or more optical signals produced from the cell being excited. The detected optical signals are provided to Field-programmable gate array (FPGA) or a computing device for analysis through an analog to digital converter (ADC), as the detected optical signals is analog. The detected analog optical signals from the APD are converted into digital data by the ADC and provided to the FPGA. The sampling rate of analog-to-digital converter (ADC) is controllable by the FPGA, which is set to 72 MHz. The FPGA controls a laser driver and the bias voltage supply to the APD's. The APD is connected to the FPGA through a digital to analog convertor (DAC). The APD's bias voltage typically ranges between 30 V and 70 V and is controlled by the FPGA to maximize the sensitivity of the detector while minimizing false detections. The laser driver controls the wavelength of the laser source to be incident on the sample solution. A power supply of 5 volts is provided to ADC and a power supply of 3.3 volts is provided to DAC and APD bias.

The APDs are used as the detector in order to have a better sensitivity. A trans-impedance amplifier is used to convert incident power to voltage. A laser driver has two channels, each capable of supplying suitable current during pulsed operation, which allows operating two different lasers at lower current, or a single laser at higher power. The number of operating lasers can be further increased by incorporating more laser driver chips. The incident light from the laser source scatters and fluoresces off an analyte attached with the cell. The scattered signals are picked up by the receiving optical channels and then fed to one or more detectors. The light reaching the detector causes a proportional current flow in the APD. The trans-impedance amplifier converts the current to a proportional voltage. The sampling rate of analog-to-digital converter (ADC) is controllable by the FPGA and is set to 72 MHz in this embodiment. The APD bias voltage typically ranges between 30 V and 70 V and it is controlled by the FPGA to maximize the sensitivity of the detector while minimizing false detections.

In an embodiment, the APD bias voltage is further boosted by the application of a second gate pulse voltage. In one embodiment, the gate pulse voltage is derived from the excitation laser source. In another embodiment, the gate pulse voltage is generated by the FPGA. The modulation of the excitation signal and gated detection helps increase the signal to noise ratio.

In an embodiment, the microfluidic flow analyzer monitors and controls the flow rates of the sample by adjusting the velocities of the sample and sheath fluids. The microfluidic flow analyzer turns on a low power infra red laser and generates a sinusoidal signal to modulate the laser. The light is detected by the receiving optical channel, placed in a straight line from the excitation optical channel. The detected light is also sinusoidally modulated. An electronic low pass filter removes optical noise and the resulting sinusoidal signal will be sent to a mixer. At the mixer, the sinusoidal signal is multiplied with another sinusoidal signal to generate a D.C voltage. When the excitation light is blocked from the collection fibre by a cell, the D.C voltage decreases. The D.C voltage is compared with a threshold voltage using a comparator, and the output of the comparator is fed to a micro controller. A second pair of optical fibres is placed further downstream of the fluid channel and the D.C voltage from that circuit is also fed to the micro controller. The micro controller has a clock that will measure the time difference between the two comparator signals and calculate the velocity of the cell. The micro controller changes the flow rates of the buffer and sample solution so that the velocity of the cell is constant.

Figure 9A:
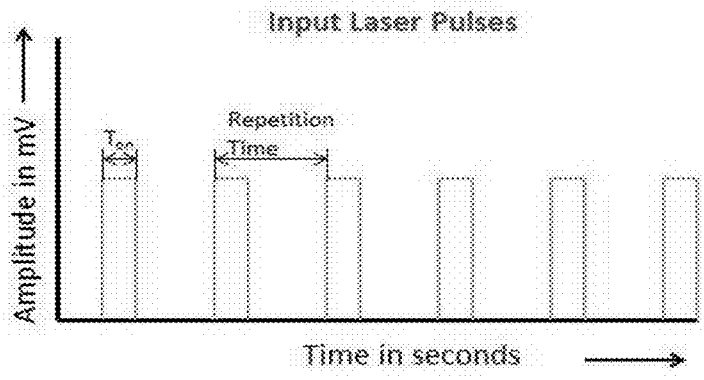
FIG. 9a shows a graph of incident laser pulses on sample solution.
Figure 9B:
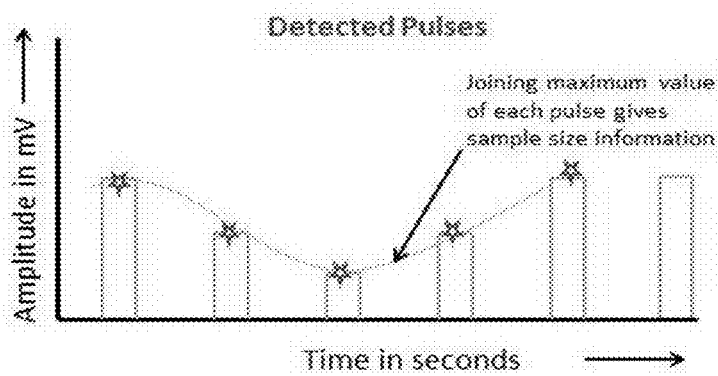
FIG. 9b shows a graph of detected pulses wherein the amplitude of the detected pulses has been reduced.

In an embodiment, the microfluidic flow analyzer turns on/off the excitation laser and detects the signal scattered in forward direction from the cell being excited, signal scattered in any other direction other than the forward direction from the cell being excited and fluorescence signal. The microfluidic flow analyzer consists of a high current driver, suitable for high power pulsed laser. A micro controller in the microfluidic flow analyzer generates a digital pulse, which is sent to the high current driver to generate a pulse of current which will then pulse the laser to create an optical pulse. Simultaneously, the microfluidic flow analyzer generates three copies of another pulse. Each copy will act as a gate pulse for the three detectors. The gate pulse for each detector is applied to the detector at the same time when the optical pulse hits the detector. The output of each detector is fed to a comparator and the voltage is compared to a threshold voltage. The output of the comparator is sent to the micro controller which logs the presence of a signal in each detector. The micro controller then sends the information for further processing to a computing device which is then presented in a graphical user interface to the user. In an embodiment, the pulse generator, comparators and analog-to-digital convertors are internal components of the micro controller. The application in the FPGA uses the laser power and the number of averages as inputs to compute and plot the detected power by the APD in mV. The modulated light from the laser source, coupled to the fiber, is incident on the central flow channel (C) through which the sample and the buffer solution under study are passed. The laser is powered for a very short time (~10 nS, repetition rate of 1 MHz) using a laser driver circuit and controlled by a digital circuit as shown in FIG. 9a. The detector signal is digitized using an analog to digital convertor (ADC). The sampling rate of the ADC is set by the FPGA. Further, reduction in noise is achieved by averaging the sampled signal every 1 µs. The laser parameters such as pulse width, power, and repetition time, the APD bias voltage, the number of averages is set by the user through a user interface. The maximum of every cycle is sent as an output. When the sample passes the laser beam, light is blocked from reaching the detector and the amplitude of the pulses reduce and the pattern is shown in the user interface canvas of FIG. 9b.

In an embodiment, a fibre Bragg grating filter is added on the receiving optical channel, so that the exciting optical channel and the receiving optical channel forms a laser cavity with higher continuous average power. The analyte attached to the cell is detected by a drop in the optical signal collected in the receiving optical channel.

Figure 10:
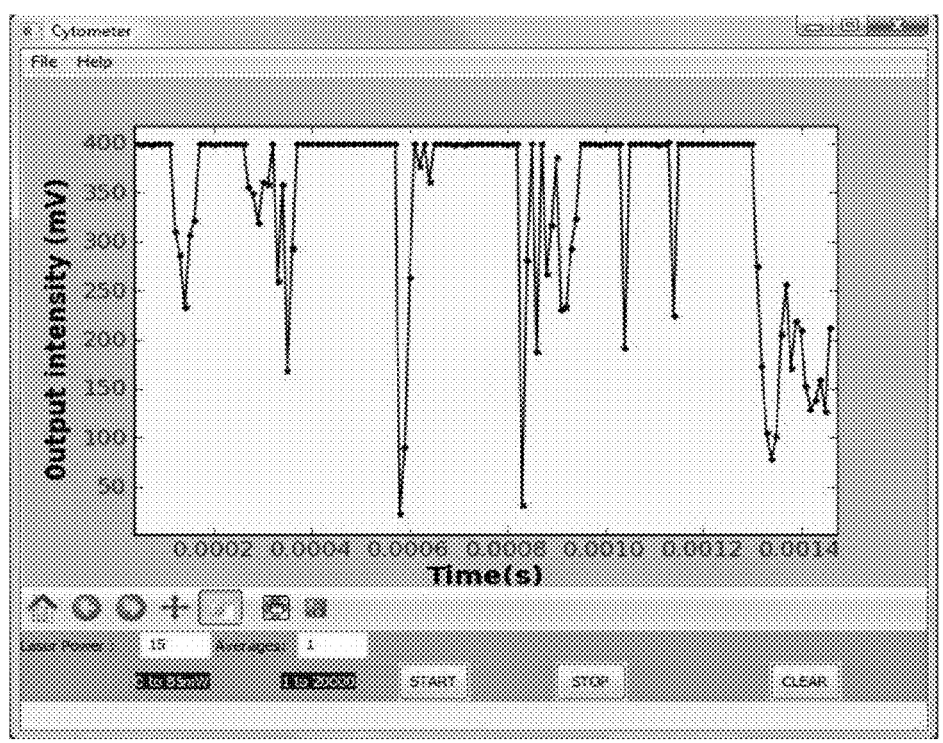
FIG. 10 illustrates a user interface for data representation of a bubble detected in accordance with an example embodiment of the present disclosure.

In order to enable continuous data acquisition, a start and a stop buttons are provided in the user interface which is shown in FIG. 10. The data shown in the plot is taken with water as sheath and air as sample. When the laser passes through the air bubble, there is a drop in the intensity of light from the saturated value. FIG. 10 illustrates a user interface for data representation of the bubble detected from the microfluidic flow analyzer using an infrared pulsed laser and single avalanche photodiode detector for forward scattering loss.

The detection speed and angle are optimized to pick up fast scattering signals from smaller size samples. The infrared laser is replaced with a visible excitation source to collect fluorescence signal along with the scattering signals.

To overcome the drawbacks mentioned in the background, the present disclosure provides a microfluidic flow analyzer which not only detects fluorescently labeled immune cells but also give quantitative information such as the level of infection. The microfluidic flow analyzer of the present disclosure, shown in FIG. 1, drastically lowers the infrastructure cost for establishment of HIV screening centers. Conventional flow cytometers range from 50-100 lakhs whereas the cost of the present miniature flow analyzer would be approximately 2-4 lakhs rupees. In turn, it would provide governments with the incentive to support the establishment of new HIV screening centers.

The microfluidic flow analyzer is not only used for HIV monitoring, but can also be utilized for a wide variety of other applications such as college models for cell counting, counting cells from background of non fluorescent cell populations and thus useful for cell culture assays, environment control, such as water contamination counter, blood count and oncological applications to detect cell proliferation.

The microfluidic flow analyzer has the advantages, such as low cost, portability, volume of samples required is low, ease of use, ease of maintenance and ease of modification and upgradability.

The microfluidic flow analyzer can be used with cheaper detector technology using PIN photodiode. Non-linear vibration spectroscopy has been integrated with microfluidic devices to detect cell size.

The current technology seeks to address the issues of high cost and lack of portability of the conventional flow cytometers for use in HIV testing. There are substantial advantages afforded by the present disclosure in comparison to current quantitative HIV detection techniques.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition, where features or aspects of the disclosure are described in terms of Markush groups, those skilled in the art will recognize that the disclosure is also thereby described in terms of any individual member or subgroup of members of the Markush group.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A microfluidic flow analyzer for pathological detection comprising:

plurality of buffer channels, wherein each of the plurality of buffer channels carries buffer solution;

a sample channel to carry sample solution;

a central flow channel configured to receive the buffer solution and the sample solution, wherein the plurality of buffer channels and the sample channel are converged at entry side of the central flow channel to form narrow path in the central flow channel for the sample solution to flow in the central flow channel;

plurality of first exciting optical channels placed orthogonally to the central flow channel, wherein each of the plurality of first exciting optical channels is coupled with a first set of fibre coupled laser source to excite cells in the sample solution, flowing through the central flow channel, to produce one or more first optical signals;

plurality of first receiving optical channels, wherein each of the plurality of first receiving optical channels is placed at a predetermined angle to optical axis of each of the plurality of first exciting optical channels respectively, to receive one of the one or more first optical signals;

plurality of first detectors, wherein each of the plurality of first detectors is placed on each of the first receiving optical channel to detect at least one of the one or more first optical signals;

one or more second exciting optical channels, wherein each of the one or more second exciting optical channels is placed at a predetermined angle to the central flow channel, each of the one or more second exciting optical channels is coupled with a second set of fibre coupled laser source to excite the cells in the sample solution, flowing through the central flow channel, to produce one or more second optical signals;

one or more second receiving optical channels, wherein each of the one or more second receiving optical channels is placed at a predetermined angle to the central flow channel to receive one of the one or more second optical signals; and one or more second detectors, wherein each of the one or more second detectors is placed on each of the one or more second receiving optical channels to detect at least one of the one or more second optical signals.

2. The microfluidic flow analyzer as claimed in claim 1 further comprises at least one infusion pump coupled to each of the plurality of buffer channels and the sample channel, wherein the at least one infusion pump controls flow rate of the buffer solution and the sample solution flowing through the plurality of buffer channels and the sample channel respectively.

3. The microfluidic flow analyzer as claimed in claim 1, wherein the plurality of buffer channels and the sample channel is configured in a microfluidic chip.

4. The microfluidic flow analyzer as claimed in claim 1 further comprises plurality of third detectors, wherein each of the plurality of third detectors is placed at:

intersection of central axis of the central flow channel and optical axis of one of the plurality of first exciting optical channels, to detect one of the one or more first optical signals scattered in any other direction other than forward direction from the excited cells; and intersection of central axis of the central flow channel and optical axis of one of the one or more second exciting optical channels, to detect one of the one or more second optical signals scattered in any other direction other than forward direction from the excited cells.

5. The microfluidic flow analyzer as claimed in claim 4, wherein each of plurality of first, second and third detectors is at least one of a fibre coupled Indium gallium arsenide (InGaAs) detector, Silicon-Photomultiplier (Si-PMT) based photo detector, silicon based photo detector and silicon avalanche photo diode.

6. The microfluidic flow analyzer as claimed in claim 1, wherein the predetermined angle at which each of the plurality of first receiving optical channels is placed at ±5 degrees to the optical axis of each of the plurality of first exciting optical channels respectively.

7. The microfluidic flow analyzer as claimed in claim 1, wherein the one or more first optical signals and the one or more second optical signals are at least one of signal scattered in a forward direction from the cell being excited, signal scattered in any other direction other than the forward direction from the cell being excited and fluorescence signal emitted from the cell being excited.

8. The microfluidic flow analyzer as claimed in claim 7, wherein the one of one or more first optical signals detected by each of the plurality of first detectors is the signal scattered in the forward direction from the cell being excited.

9. The microfluidic flow analyzer as claimed in claim 7, wherein the one of the one or more second detectors detects the fluorescence signal from the one or more second optical signals, when the one of the one or more second receiving optical channels is placed orthogonally to the central flow channel.

10. The microfluidic flow analyzer as claimed in claim 7, wherein the one of the one or more second detectors detects the signal scattered in any other direction other than forward direction from the cell being excited, when the one of the one or more second receiving optical channels is placed at an angle of 45 degrees to the central flow channel.

11. The microfluidic flow analyzer as claimed in claim 7, wherein the one of the one or more second detector detects the signal scattered in any other direction other than forward direction from the cell being excited, when the one of the one or more second receiving optical channels is placed at an angle of ±40 degrees to the central flow channel.

12. The microfluidic flow analyzer as claimed in claim 1, wherein the first set of fibre coupled laser source coupled with each of the plurality of first exciting optical channels and the second set of fibre coupled laser source coupled with each of the one or more second exciting optical channels is terminated at a lensed fibre.

13. The microfluidic flow analyzer as claimed in claim 1, wherein one of the one or more second receiving optical channels is configured with a Fibre Bragg grating to filter laser light emitted from each of the one or more second exciting optical channels.

14. The microfluidic flow analyzer as claimed in claim 1, wherein the predetermined angle at which each of the one or more second exciting optical channels is placed is in a range of 40 degrees to 90 degrees.

15. The microfluidic flow analyzer as claimed in claim 1, wherein the predetermined angle at which each of the one or more second receiving optical channels is placed is in a range of 40 degrees to 90 degrees.

16. The microfluidic flow analyzer as claimed in claim 1 further comprises at least one waste reservoir (W) to collect waste samples after analysis from the central flow channel.

17. The microfluidic flow analyzer as claimed in claim 1 further comprises a computing unit being capable of:
receiving the one or more first optical signals detected by each of the plurality of first optical detectors and each of plurality of the third optical detectors;
receiving the one or more second optical signals detected by each of the plurality of second optical detectors and each of the plurality of third optical detectors; and
analyzing the received one or more first optical signals and the one or more second optical signals for the pathological detection.

18. A method for pathological detection using a microfluidic flow analyzer comprising:
receiving buffer solution and sample solution by a central flow channel through plurality of buffer channels and a sample channel respectively, wherein the plurality of buffer channels and the sample channel are converged at entry side of the central flow channel to form narrow path in the central flow channel for the sample solution to flow in the central flow channel;
exciting cells in the sample solution flowing through the central flow channel by plurality of first set of fibre coupled laser source to produce one or more first optical signals, wherein the plurality of first set of fibre coupled laser source is respectively coupled to plurality of first exciting optical channels;
detecting one of the one or more first optical signals by plurality of first detectors, wherein each of the plurality of first detectors is placed on each of plurality of first receiving optical channels respectively;
receiving the detected one of the one or more first optical signals by a computing unit for pathological detection;
exciting cells in the sample solution by plurality of second set of fibre coupled laser source to produce one or more second optical signals, wherein the plurality of second set of fibre coupled laser source is respectively coupled to one or more second exciting optical channels;
detecting at least one of the one or more second optical signals by one or more second detectors, wherein each of the one or more second detectors is placed on one or more second receiving optical channels respectively; and
receiving the detected at least one of the one or more second optical signals by the computing unit for pathological detection.

19. The method as claimed in claim 18, wherein the one or more first optical signals and the one or more second optical signals are at least one of signal scattered in a forward direction from the cell being excited, signal scattered in any other direction other than the forward direction from the cell being excited and fluorescence signal emitted from the cell being excited.

20. The method as claimed in claim 18, wherein one of the one or more second detectors detects the fluorescence signal from the one or more second optical signals, when one of the one or more second receiving optical channels is placed orthogonally to the central flow channel, further wherein the
the one or more second detectors detects the signal scattered in any other direction other than forward direction from the excited cell, when one of the one or more second receiving optical channels is placed at an angle of 45 degrees to the central flow channel, further wherein the
one of the one or more second detectors detects the signal scattered in any other direction other than forward direction from the excited cell, when one of the one or more second receiving optical channels is placed at an angle of ±40 degrees to the central flow channel.

* * * * *